(12) United States Patent
Tanaka et al.

(10) Patent No.: US 11,235,317 B2
(45) Date of Patent: Feb. 1, 2022

(54) TUBULAR INSTRUMENT AND MANIPULATION SYSTEM

(71) Applicant: NSK LTD., Tokyo (JP)

(72) Inventors: Nobuaki Tanaka, Kanagawa (JP); Sumio Sugita, Kanagawa (JP); Richard House, Kanagawa (JP)

(73) Assignee: NSK LTD., Tokyo (JP)

( * ) Notice: Subject to any disclaimer, the term of this patent is extended or adjusted under 35 U.S.C. 154(b) by 264 days.

(21) Appl. No.: 16/483,112

(22) PCT Filed: Feb. 5, 2018

(86) PCT No.: PCT/JP2018/003832
§ 371 (c)(1),
(2) Date: Aug. 2, 2019

(87) PCT Pub. No.: WO2018/163687
PCT Pub. Date: Sep. 13, 2018

(65) Prior Publication Data
US 2019/0381495 A1   Dec. 19, 2019

(30) Foreign Application Priority Data

Mar. 10, 2017  (JP) .............................. JP2017-046565

(51) Int. Cl.
*B01L 3/02*      (2006.01)
*B25J 7/00*      (2006.01)
(Continued)

(52) U.S. Cl.
CPC ............. *B01L 3/021* (2013.01); *B01L 3/0286* (2013.01); *B25J 7/00* (2013.01); *C12M 1/265* (2013.01); *C12M 3/00* (2013.01); *G02B 21/0004* (2013.01)

(58) Field of Classification Search
CPC .......... B01L 3/021; B01L 3/0286; B25J 7/00; C12M 1/265; C12M 3/00; G02B 21/0004
See application file for complete search history.

(56) References Cited

U.S. PATENT DOCUMENTS

2006/0182662 A1    8/2006 Dean
2012/0301960 A1*  11/2012 Aten .................. C12N 15/89
                                              435/375
(Continued)

FOREIGN PATENT DOCUMENTS

CN      204958919 U    1/2016
JP       10-54709 A    2/1998
(Continued)

OTHER PUBLICATIONS

Notification of Reasons for Refusal of Japanese Application No. 2018-553489 dated Nov. 5, 2018.
(Continued)

*Primary Examiner* — William H. Beisner
*Assistant Examiner* — Danielle B Henkel
(74) *Attorney, Agent, or Firm* — Sughrue Mion, PLLC

(57) ABSTRACT

A collection pipette that collects a microscopic object includes a first tube part, a second tube part connected to an end of the first tube part, and a third tube part connected to the other end of the first tube part. The longitudinal direction of the third tube part intersects with the longitudinal direction of the first tube part, and is parallel to the longitudinal direction of the second tube part. For example, the length in the longitudinal direction of the third tube part is shorter than the length in the longitudinal direction of the first tube part.

4 Claims, 11 Drawing Sheets

(51) Int. Cl.
  *C12M 1/26*  (2006.01)
  *C12M 3/00*  (2006.01)
  *G02B 21/00* (2006.01)

(56) References Cited

U.S. PATENT DOCUMENTS

2013/0023052 A1* 1/2013 Tanaka .................. G02B 21/32
                                                    435/461
2017/0001302 A1* 1/2017 Nomura .................... B25J 7/00

FOREIGN PATENT DOCUMENTS

| | | |
|---|---|---|
| JP | 2005-224194 A | 8/2005 |
| JP | 2006-292468 A | 10/2006 |
| JP | 2007-504816 A | 3/2007 |
| JP | 2010-200679 A | 9/2010 |
| JP | 2011-172533 A | 9/2011 |
| JP | 2013-169185 A | 9/2013 |
| JP | 2017-023049 A | 2/2017 |
| JP | 2018-068169 A | 5/2018 |
| WO | 2005/023124 A2 | 3/2005 |
| WO | 2016/051563 A1 | 4/2016 |

OTHER PUBLICATIONS

International Search Report for PCT/JP2018/003832 dated May 1, 2018 (PCT/ISA/210).

* cited by examiner

TUBULAR INSTRUMENT AND MANIPULATION SYSTEM

CROSS REFERENCE TO RELATED APPLICATIONS

This application is a National Stage of International Application No. PCT/JP2018/003832 filed Feb. 5, 2018, claiming priority based on Japanese Patent Application No. 2017-046565 filed Mar. 10, 2017.

FIELD

The present invention relates to a tubular instrument and a manipulation system.

BACKGROUND

In the field of biotechnology, a micromanipulation system for finely manipulating microscopic objects used when DNA solution or a cell is injected into a cell or an egg under microscopic observations has been known. Patent Literature 1 discloses a cell collection apparatus including a manipulator for sucking cells. Moreover, Patent Literature 2 discloses a cell culture dish the surface of which is provided with a plurality of microcontainers with different sizes.

CITATION LIST

Patent Literature

Patent Literature 1: Japanese Patent Application Laid-open No. 2013-169185 A
Patent Literature 2: Japanese Patent Application Laid-open No. 2010-200679 A

SUMMARY

Technical Problem

In the container holding liquid, a meniscus is generated at the boundary between the inner wall of the container and the liquid surface. A meniscus is also generated at the boundary between the surface of the pipette and the liquid surface, when the tip end part of the pipette is immersed in the liquid. Thus, when an operator is observing the tip end of the pipette by using a microscope disposed above the container, the meniscus may enter the visual field of the microscope. When the meniscus is overlapped with the tip end of the pipette, the operator cannot clearly observe the tip end of the pipette. Consequently, there is a possibility of reducing the operability of the manipulation.

The present invention has been made in view of the above problems, and an object of the present invention is to provide a tubular instrument and a manipulation system with high operability.

Solution to Problem

A tubular instrument according to one embodiment of the present invention that collects a microscopic object is disclosed. The tubular instrument includes a first tube part, a second tube part connected to an end of the first tube part, and a third tube part connected to another end of the first tube part. A longitudinal direction of the third tube part intersects with a longitudinal direction of the first tube part, and is parallel to a longitudinal direction of the second tube part. Consequently, it is possible to generate a meniscus on the surface of the first tube part, when the third tube part is immersed in liquid.

As a desirable embodiment of the present invention, a length in the longitudinal direction of the third tube part is shorter than that in the longitudinal direction of the first tube part.
Consequently, it is possible to easily dispose the third tube part in the container for holding the microscopic objects.

As a desirable embodiment of the present invention, the first tube part includes a first portion placed at a side of the end, and a second portion placed at a side of the other end, and an outer diameter of the second portion is smaller than an outer diameter of the first portion. Consequently, it is possible to reduce the size of the meniscus formed on the surface of the first tube part, by disposing the second portion at the position overlapping with the liquid surface.

A manipulation system according to one embodiment of the present invention includes the tubular instrument described above, a manipulator fitted with the tubular instrument, a sample stage on which a container for holding the microscopic object is mounted, and a first microscope disposed above the sample stage. Consequently, the operator can observe the third tube part from above while enlarging the third tube part using the first microscope.

As a desirable embodiment of the present invention, the manipulation system further includes a second microscope disposed at a side of the sample stage. Consequently, the operator can observe the third tube part from the side while enlarging the third tube part using the second microscope.

As a desirable embodiment of the present invention, the manipulation system further includes a first image pickup device that picks up an image of the third tube part through the first microscope, a second image pickup device that picks up an image of the third tube part through the second microscope, and a display unit that displays a first image picked up by the first image pickup device, and a second image picked up by the second image pickup device. Consequently, the display unit can display the first image that indicates the enlarged third tube part from above, and the second image that indicates the enlarged third tube part from the side.

As a desirable embodiment of the present invention, the manipulation system further includes a storage unit that stores therein the first image and the second image in an associated manner based on an image pickup time. Consequently, the display unit can reproduce and display side by side the first image and the second image that are picked up at the same time.

As a desirable embodiment of the present invention, the manipulation system further includes a third image pickup device that picks up an image of a side of the sample stage from a third direction that intersects with a first direction picked up by the first image pickup device and a second direction picked up by the second image pickup device. The display unit displays a third image picked up by the third image pickup device. Consequently, the display unit can display the third image that is an image of the sample stage side picked up from an upper oblique direction of the sample stage, side by side with the first image and the second image. It is possible to easily take a bird's eye view of the sample stage and the surroundings from the third image.

A manipulation system according to one embodiment of the present invention that collects a microscopic object using a tubular instrument is disclosed. The manipulation system includes a manipulator fitted with the tubular instrument, a sample stage on which a container for holding the microscopic object is mounted, a first microscope disposed above the sample stage, a first image pickup device that picks up an image of the tubular instrument through the first microscope, a second microscope disposed at a side of the sample stage, a second image pickup device that picks up an image of the tubular instrument through the second microscope, and a display unit that displays a first image picked up by the first image pickup device, and a second image picked up by the second image pickup device. Consequently, the display unit can display the third tube part from above and the side, while enlarging the third tube part. Thus, the operator can clearly observe the tip end of the pipette.

Advantageous Effects of Invention

According to the present invention, it is possible to provide the tubular instrument and the manipulation system with high operability.

DESCRIPTION OF EMBODIMENTS

Hereinafter, a mode for carrying out the invention (hereinafter, referred to as an embodiment) will be described in detail with reference to the accompanying drawings. It is to be understood that the present invention is not limited to the following embodiment. Moreover, components in the following embodiment include components that can be easily assumed by a person skilled in the art, components being substantially the same as those embodiments, and components that fall within what is called the range of equivalents. Furthermore, the components disclosed in the following embodiment may be combined with one another as appropriate.

Figure 1:
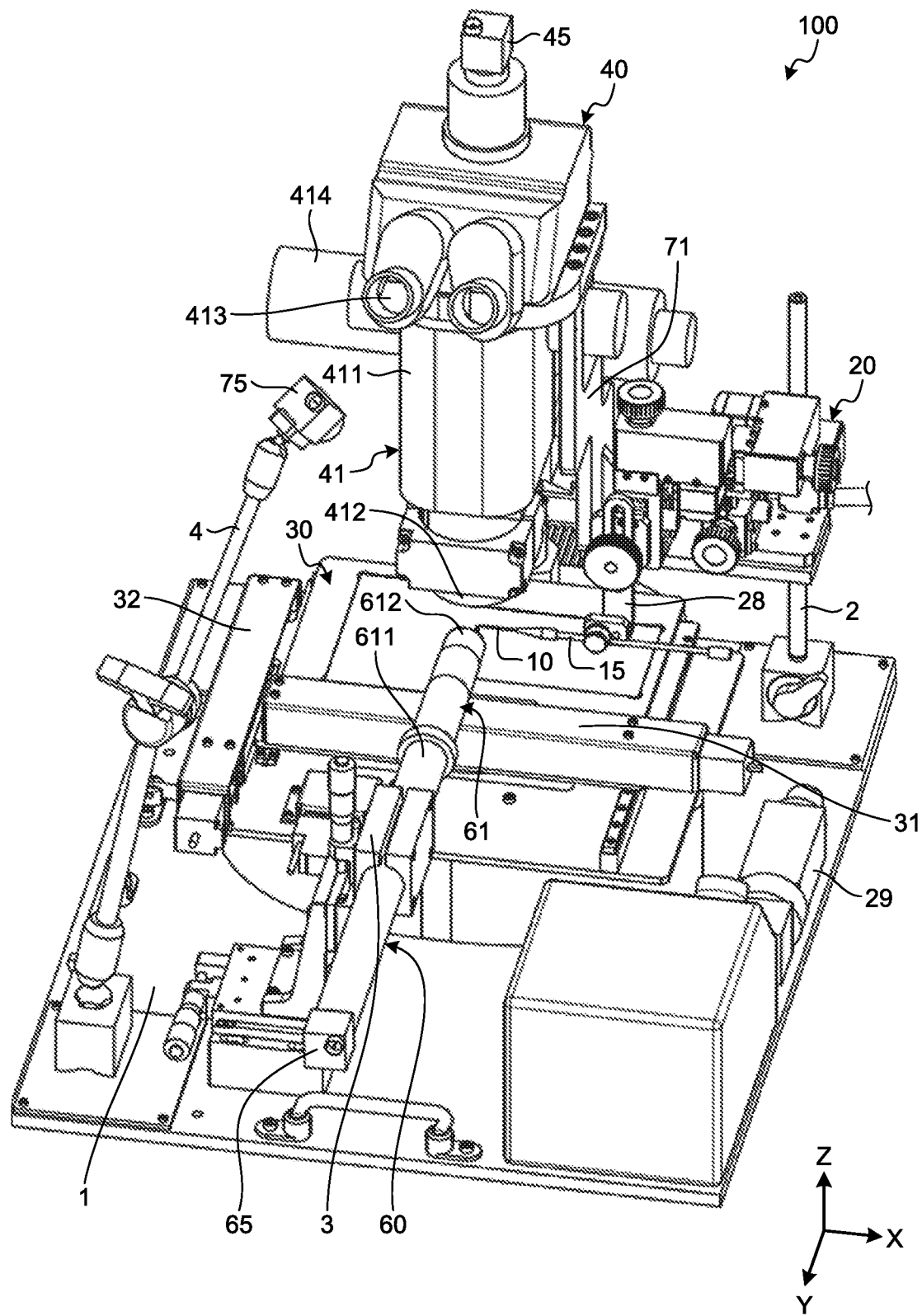
FIG. 1 is a perspective view illustrating a configuration example of a manipulation system according to an embodiment.
Figure 2:
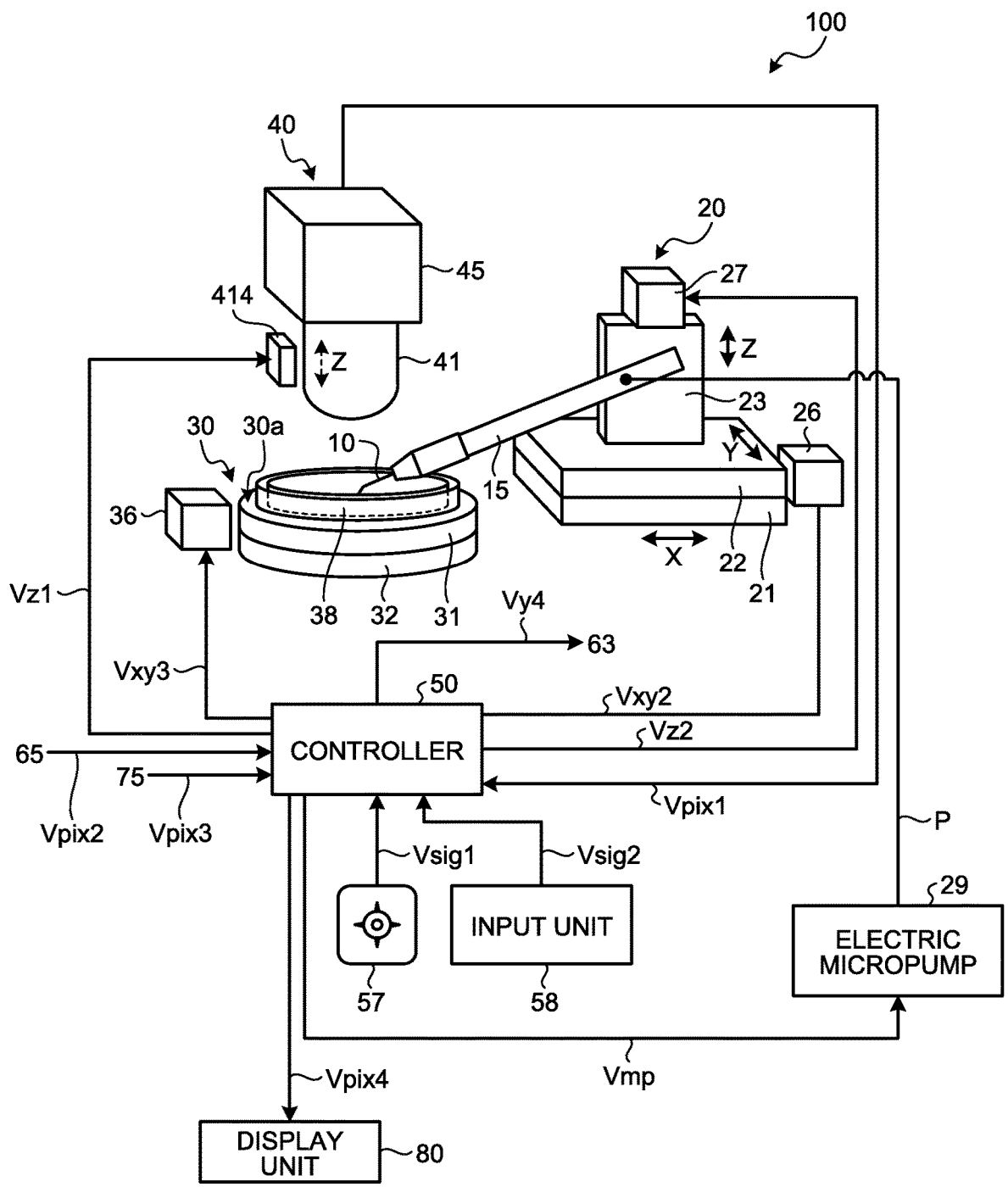
FIG. 2 is a schematic view illustrating a configuration example of the manipulation system according to the embodiment.

FIG. 1 is a perspective view illustrating a configuration example of a manipulation system according to an embodiment. FIG. 2 is a schematic view illustrating a configuration example of the manipulation system according to the embodiment. A manipulation system 100 illustrated in FIG. 1 and FIG. 2 is a device that separates a desirable microscopic object one by one, from a plurality of microscopic objects held in a container 38. For example, the microscopic object is a cell.

As illustrated in FIG. 1 and FIG. 2, the manipulation system 100 includes a base 1, a collection pipette 10, a pipette holding unit 15, a manipulator 20, a sample stage 30, a first microscope unit 40 including a first image pickup device 45, a controller 50, a second microscope unit 60 including a second image pickup device 65, a third image pickup device 75, a joy stick 57, an input unit 58, and a display unit 80. In the present embodiment, a direction parallel to a mounting surface 30a of the sample stage 30 is the X-axis direction. A direction that is parallel to the mounting surface 30a and that is perpendicular to the X-axis direction is the Y-axis direction. The normal direction of the mounting surface 30a is the Z-axis direction. The mounting surface 30a is a horizontal plane parallel to the base 1.

The collection pipette 10 is a tubular instrument for collecting cells. For example, the collection pipette 10 is formed in a needle shape, and the material of which is glass. An opening part for collecting cells is provided at the tip end of the collection pipette 10. The details of the collection pipette 10 will be described below with reference to FIG. 6 to FIG. 8.

The pipette holding unit 15 is a tubular instrument for holding the collection pipette 10. For example, the material of the pipette holding unit 15 is glass or metal. An end of the pipette holding unit 15 is coupled to the collection pipette 10. Moreover, the other end of the pipette holding unit 15 is connected to an electric micropump 29 included in the manipulator 20. The internal pressure of the pipette holding unit 15 and the collection pipette 10 is reduced or increased by pressure P supplied from the electric micropump 29. When the internal pressure of the collection pipette 10 is lower than the normal pressure, the collection pipette 10 can collect cells by sucking the cells from the opening part at the tip end. The pipette holding unit 15 is coupled to the manipulator 20 via a coupling unit 28, which will be described below.

The manipulator 20 is a device for moving the pipette holding unit 15 and the collection pipette 10 in the X-axis direction, the Y-axis direction, and the Z-axis direction. Moreover, the manipulator 20 is a device for moving the first microscope unit 40 in the X-axis direction, the Y-axis direction, and the Z-axis direction. The manipulator 20 is fixed to the base 1 via a fixing tool 2.

The manipulator 20 includes an X-axis table 21, a Y-axis table 22, a Z-axis table 23, driving devices 26 and 27, coupling units 28 and 71, and the electric micropump 29. The X-axis table 21 moves in the X-axis direction, when the driving device 26 is driven. The Y-axis table 22 moves in the Y-axis direction, when the driving device 26 is driven. The Z-axis table 23 moves in the Z-axis direction, when the driving device 27 is driven. The driving devices 26 and 27, and the electric micropump 29 are connected to the controller 50.

The coupling unit 28 couples the pipette holding unit 15 to the manipulator 20. Moreover, the coupling unit 71 couples a lens barrel 411 of the first microscope unit 40 to the manipulator 20. For example, the coupling units 28 and 71 are made of metal. For example, the coupling units 28 and 71 are fitted to the Z-axis table 23. Consequently, the pipette holding unit 15 and the first microscope unit 40 can move in the Z-axis direction as far as the Z-axis table 23, with the movement of the Z-axis table 23.

Moreover, in the manipulator 20, the Z-axis table 23 is fitted on the Y-axis table 22. Consequently, the pipette holding unit 15 and the first microscope unit 40 can move in the Y-axis direction as far as the Y-axis table 22, with the movement of the Y-axis table 22. Furthermore, the Y-axis table 22 is fitted on the X-axis table 21. Consequently, the pipette holding unit 15 and the first microscope unit 40 can move in the X-axis direction as far as the X-axis table 21, with the movement of the X-axis table 21. In this manner, the pipette holding unit 15 and the first microscope unit 40 can move in the X-axis direction, the Y-axis direction, and the Z-axis direction with the operation of the manipulator 20.

The sample stage 30 supports the container 38. For example, the container 38 is mounted on the mounting surface 30a of the sample stage 30. For example, the container 38 is a petri dish or a dish. The sample stage 30 includes an X-axis stage 31, a Y-axis stage 32, and a driving device 36. The X-axis stage 31 moves in the X-axis direction, when the driving device 36 is driven. The Y-axis stage 32 moves in the Y-axis direction, when the driving device 36 is driven. The X-axis stage 31 is fitted on the Y-axis stage 32. The driving device 36 is connected to the controller 50.

In FIG. 2, the shape of the sample stage 30 in a plan view (hereinafter, referred to as a planar shape) is a circular shape. However, the planar shape of the sample stage 30 is not limited to the circular shape, but may also be a rectangular shape, for example. Moreover, in FIG. 2, the planar shape of the container 38 is a circular shape. However, the planar shape of the container 38 is not limited to the circular shape, but may also be a rectangular shape, for example. Furthermore, in FIG. 2, a single container 38 is mounted on the sample stage 30. However, the number of the container 38 to be mounted on the sample stage 30 is not limited to one but may also be plural.

The first microscope unit 40 is disposed above the sample stage 30. The first microscope unit 40 includes a first microscope 41, the first image pickup device 45, and a light source (not illustrated) that emits light toward the mounting surface 30a of the sample stage 30. The first microscope 41 includes the lens barrel 411, an objective lens 412, an eyepiece lens 413, and a driving device 414. The first microscope 41 is a stereoscopic microscope in which the objective lens 412 is placed above the container 38. The objective lens 412 moves in the Z-axis direction, when the driving device 414 is driven. Consequently, the focal position of the first microscope 41 can be adjusted. A plurality of types of the objective lenses 412 may be prepared according to desired magnification. Moreover, for example, the first image pickup device 45 includes a solid-state image pickup device such as a complementary metal oxide semiconductor (CMOS) image sensor or a charge-coupled device (CCD) image sensor. The first image pickup device 45 can pick up an image of the tip end of the collection pipette 10 from the Z-axis direction through the first microscope 41.

The second microscope unit 60 is disposed at the side of the sample stage 30. The second microscope unit 60 includes a second microscope 61 and the second image pickup device 65. The second microscope 61 includes a lens barrel 611 and an objective lens 612. For example, the second image pickup device 65 includes a solid-state image pickup device such as a CMOS image sensor or a CCD image sensor. The second image pickup device 65 can pick up an image of the tip end of the collection pipette 10 from the Y-axis direction through the second microscope 61. The second microscope unit 60 is fixed to the base 1 via a fixing tool 3.

The third image pickup device 75 is fixed to the base 1 via a fixing tool 4. The fixing tool 4 can move in the X-axis direction and the Y-axis direction, and can extend in the Z-axis direction. Consequently, the third image pickup device 75 can pick up an image of the sample stage 30 side from an upper oblique direction of the sample stage 30 that intersects with the X-axis direction, the Y-axis direction, and the Z-axis direction.

The input unit 58 is a keyboard, a touch panel, and the like. The joy stick 57 and the input unit 58 are connected to the controller 50. The operator can input a command to the controller 50 with the joy stick 57 and the input unit 58.

Figure 3:
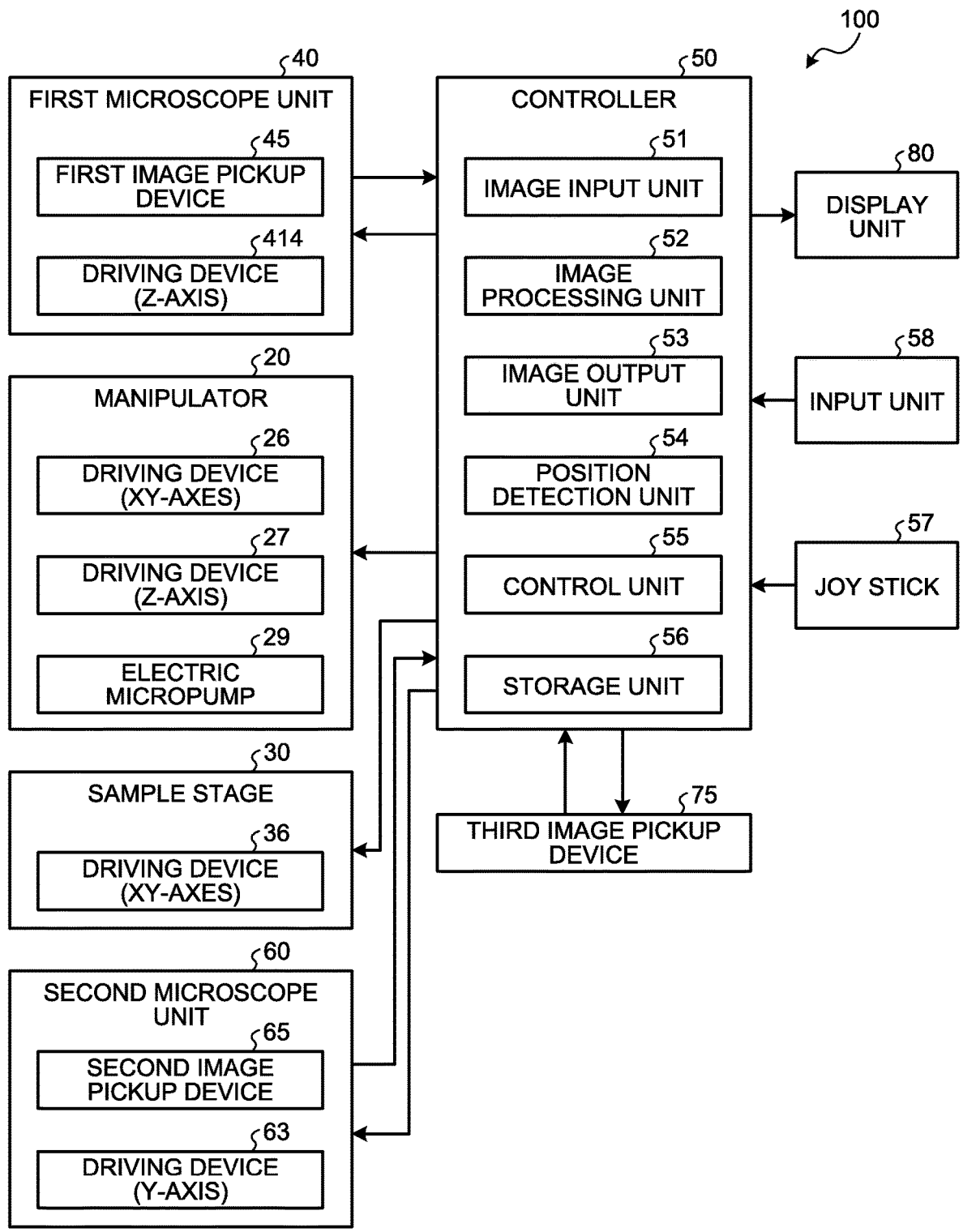
FIG. 3 is a block diagram illustrating a configuration example of the manipulation system according to the embodiment.

Next, functions of the controller 50 will be described with reference to FIG. 3. FIG. 3 is a block diagram illustrating a configuration example of the manipulation system according to the embodiment. The controller 50 includes hardware resources such as a central processing unit (CPU) serving as a calculation means, and a hard disk, a random-access memory (RAM), a read-only memory (ROM), and the like serving as a storage means.

As illustrated in FIG. 3, as the functions, the controller 50 includes an image input unit 51, an image processing unit 52, an image output unit 53, a position detection unit 54, a control unit 55, and a storage unit 56. The image input unit 51, the image processing unit 52, the image output unit 53, the position detection unit 54, and the control unit 55 are implemented by the calculation means described above. The storage unit 56 is implemented by the storage means described above. The controller 50 performs various kinds of calculations on the basis of programs stored in the storage unit 56, and outputs a driving signal such that the control unit 55 performs various types of controls according to the calculation results.

The control unit 55 controls the driving device 414 of the first microscope unit 40, the driving devices 26 and 27 and the electric micropump 29 of the manipulator 20, the driving device 36 of the sample stage 30, and a driving device 63 of the second microscope unit 60. The control unit 55 supplies driving signals Vz1, Vxy2, Vz2, Vxy3, and Vy4 (see FIG. 2) to the driving devices 414, 26, 27, 36, and 63, respectively. Moreover, the control unit 55 supplies a driving signal Vmp (see FIG. 2) to the electric micropump 29. It is to be noted that the control unit 55 may also supply the driving signals Vz1, Vxy2, Vz2, Vxy3, Vy4, and Vmp via a driver, an amplifier, and the like provided according to the needs.

A first image signal Vpix1 (see FIG. 2) output from the first image pickup device 45, a second image signal Vpix2 (see FIG. 2) output from the second image pickup device 65, and a third image signal Vpix3 (see FIG. 2) output from the third image pickup device 75 are supplied to the image input unit 51. The image processing unit 52 receives the first image signal Vpix1, the second image signal Vpix2, and the third image signal Vpix3 from the image input unit 51, and performs image processing. The image output unit 53 outputs image information of an image processed by the image processing unit 52 to the storage unit 56 and the display unit 80.

For example, the first image signal Vpix1 includes a first image picked up by the first image pickup device 45 through the first microscope 41, and the image pickup time. The first image is a moving image. Similarly, the second image signal Vpix2 includes a second image picked up by the second image pickup device 65 through the second microscope 61, and the image pickup time. The second image is also a moving image. The third image signal Vpix3 includes a third image picked up by the third image pickup device 75, and the image pickup time. The third image is also a moving image.

The image processing unit 52 associates the first image signal Vpix1, the second image signal Vpix2, and the third image signal Vpix3 with one another on the basis of the image pickup time, and generates an edited image signal Vpix4. An edited image is included in the edited image signal Vpix4. The edited image is a moving image in which the first image, the second image, and the third image that are picked up at the same time are arranged and displayed side by side. The image output unit 53 outputs the first image signal Vpix1, the second image signal Vpix2, the third image signal Vpix3, and the edited image signal Vpix4 to the storage unit 56.

Figure 4:
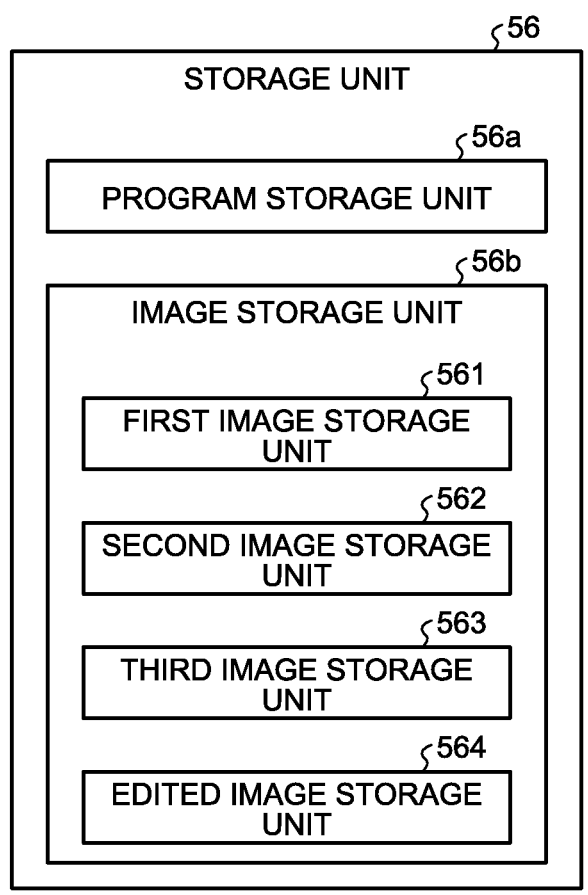
FIG. 4 is a block diagram illustrating a configuration example of a storage unit.

FIG. 4 is a block diagram illustrating a configuration example of a storage unit. As illustrated in FIG. 4, as the functions, the storage unit 56 includes a program storage unit 56a that stores therein a program for operating the manipulation system 100, and an image storage unit 56b that stores therein an image signal. The image storage unit 56b includes a first image storage unit 561 that stores therein the first image signal Vpix1, a second image storage unit 562 that stores therein the second image signal Vpix2, a third image storage unit 563 that stores therein the third image signal Vpix3, and an edited image storage unit 564 that stores therein the edited image signal Vpix4.

Moreover, the image output unit 53 outputs at least one or more image signal among the first image signal Vpix1, the second image signal Vpix2, the third image signal Vpix3, and the edited image signal Vpix4, to the display unit 80. For example, a control signal Vsig1 is output to the controller 50 from the joy stick 57, when the operator operates the joy stick 57.

The image output unit 53 selects an image signal to be output to the display unit 80 according to the control signal Vsig1 supplied to the controller 50, and outputs the image signal to the display unit 80. Alternatively, a control signal Vsig2 may be output to the controller 50 from the input unit 58, when the operator operates the input unit 58. The image output unit 53 may also select an image signal to be output to the display unit 80 according to the control signal Vsig2 supplied to the controller 50, and output the image signal to the display unit 80.

The position detection unit 54 receives image information from the image processing unit 52, and can detect the position of a cell on the basis of the received image information. When the position detection unit 54 detects the position of the cell, the position detection unit 54 can reflect the detection result to the image information. For example, when the position detection unit 54 detects the position of a cell, the image processing unit 52 may also edit the image information such that the position of the cell is indicated by an arrow.

Figure 5:
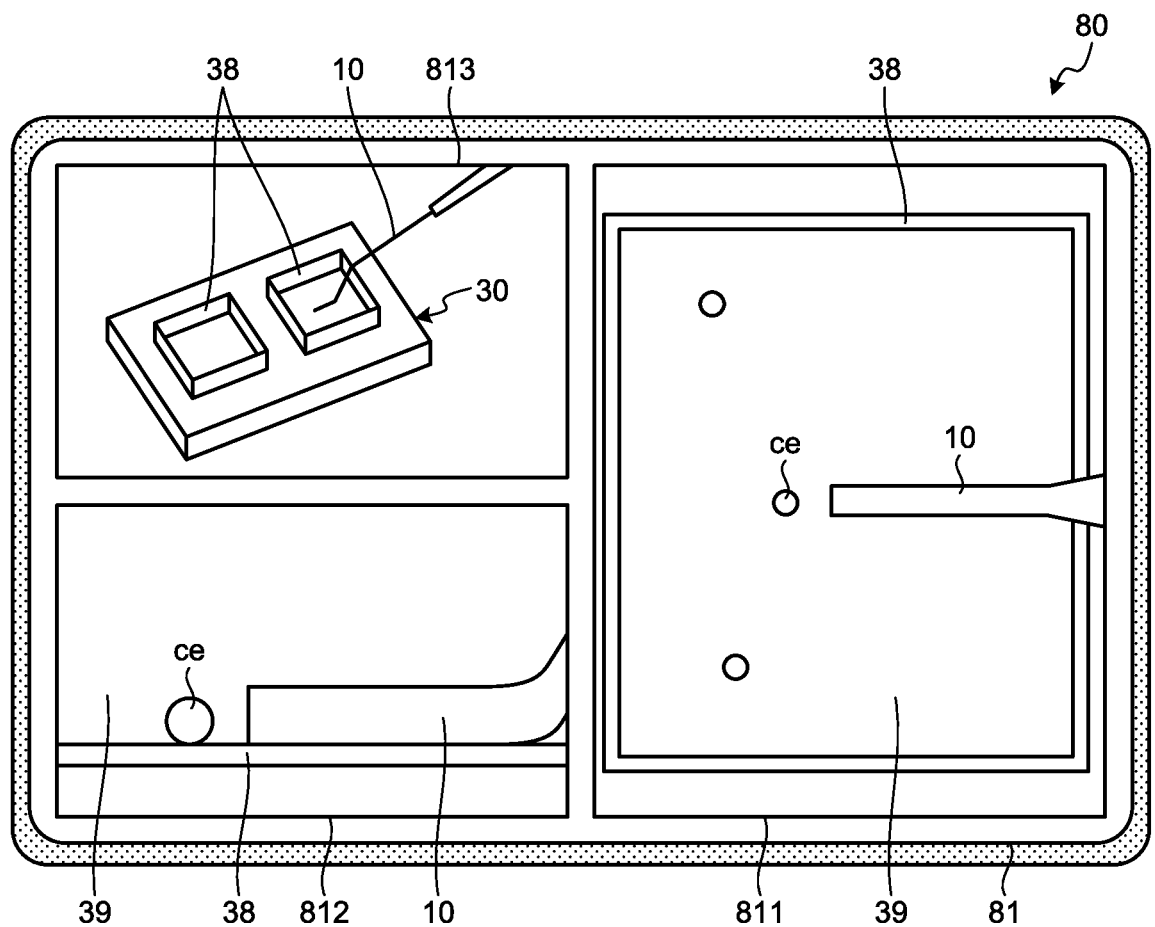
FIG. 5 is a diagram illustrating an example of an image to be displayed on a screen of a display unit.

For example, the display unit 80 is a liquid-crystal panel and the like. The display unit 80 is connected to the controller 50. FIG. 5 is a diagram illustrating an example of a screen of a display unit. FIG. 5 illustrates a case when an edited image is displayed on a screen 81 of the display unit 80. In the edited image, a first image 811, a second image 812, and a third image 813 that are picked up at the same timing are arranged side by side. The display unit 80 may display the edited image in real time or substantially in real time, or may read out an edited image stored in the edited image storage unit 564 and reproduce and display the edited image. The image displayed on the screen 81 can be switched, when the operator operates the joy stick 57 or the input unit 58. Moreover, the edited image (moving image) displayed on the screen 81 can be temporarily stopped, when the operator operates the joy stick 57 or the input unit 58. The image displayed on the screen 81 is not limited to the edited image, and may only be the first image 811, the second image 812, or the third image 813.

Figure 6:
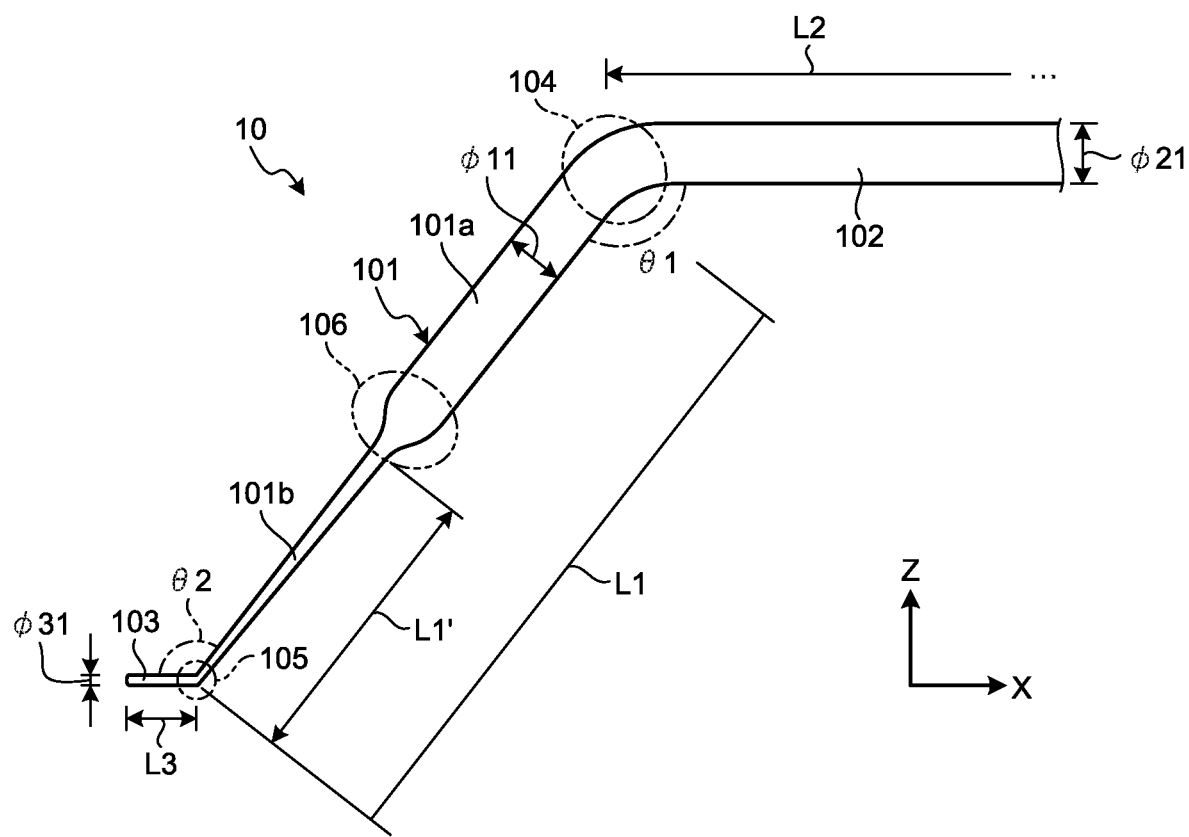
FIG. 6 is a side view illustrating a configuration example of a collection pipette according to the embodiment.
Figure 7:
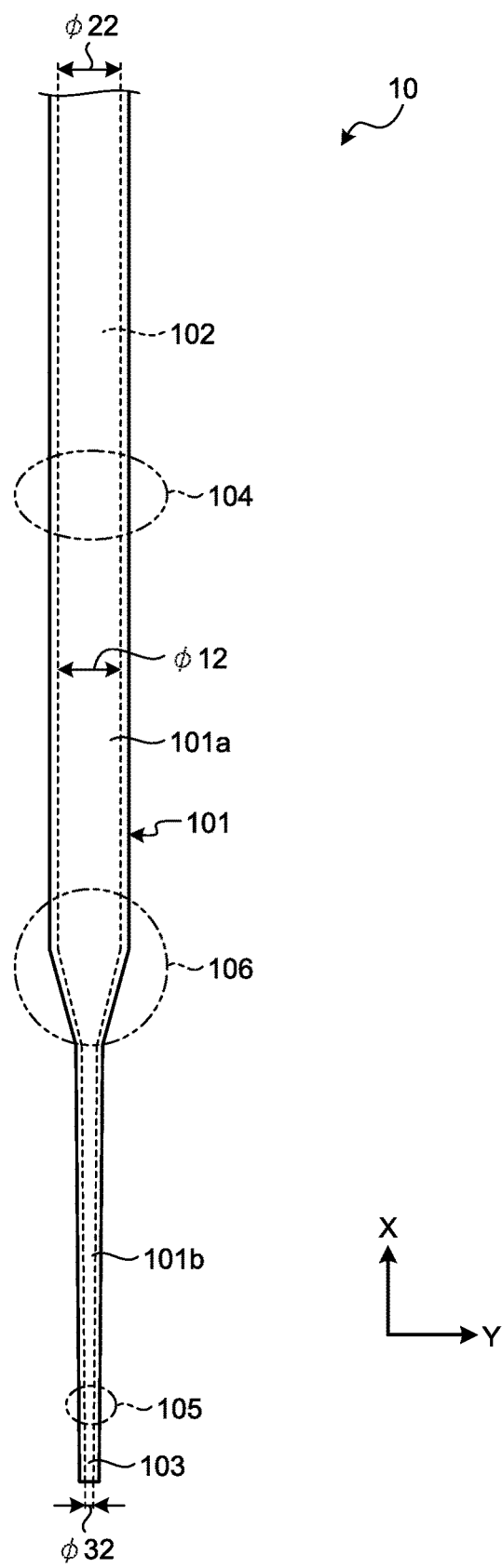
FIG. 7 is a plan view illustrating a configuration example of the collection pipette according to the embodiment.

FIG. 6 is a side view illustrating a configuration example of a collection pipette according to the embodiment. FIG. 7 is a plan view illustrating a configuration example of the collection pipette according to the embodiment. As illustrated in FIG. 6 and FIG. 7, the collection pipette 10 is a glass needle having a shape bent in two stages. More specifically, the collection pipette 10 includes a first tube part 101, a second tube part 102 connected to an end of the first tube part 101, and a third tube part 103 connected to the other end of the first tube part 101. The second tube part 102 is a portion at the side held by the pipette holding unit 15. The third tube part 103 is a tip end part of the collection pipette 10 and is a portion at the side for collecting microscopic objects such as a cell. The first tube part 101, the second tube part 102, and the third tube part 103 each linearly extend in one direction.

A first bending part 104 is present between the first tube part 101 and the second tube part 102. A second bending part 105 is present between the first tube part 101 and the third tube part 103. The longitudinal direction of the first tube part 101 and the longitudinal direction of the second tube part 102 are intersected with each other. The longitudinal direction of the first tube part 101 and the longitudinal direction of the third tube part 103 are also intersected with each other. The longitudinal direction of the second tube part 102 and the longitudinal direction of the third tube part 103 are parallel or substantially parallel to each other. For example, it is assumed that an obtuse angle between the longitudinal direction of the first tube part 101 and the longitudinal direction of the second tube part 102 (hereinafter, referred to as a bending angle of the first bending part 104) is θ1. It is assumed that an obtuse angle between the longitudinal direction of the first tube part 101 and the longitudinal direction of the third tube part 103 (hereinafter, referred to as a bending angle of the second bending part 105) is θ2. An absolute value |θ1−θ2| of a difference between the bending angle θ1 of the first bending part 104 and the bending angle θ2 of the second bending part 105 is equal to or more than 0° and less than 5°.

Moreover, when the length in the longitudinal direction of the first tube part 101 is L1, the length in the longitudinal direction of the second tube part 102 is L2, and the length in the longitudinal direction of the third tube part 103 is L3, it is L3<L1 and L3<L2. Consequently, it is possible to easily dispose the third tube part 103 that is the tip end part of the collection pipette 10 in the container 38.

The shape of the first tube part 101 cut by a plane perpendicular to the longitudinal direction of the first tube part 101 is a circular shape. Similarly, the shape of the second tube part 102 cut by a plane perpendicular to the longitudinal direction of the second tube part 102 is a circular shape. The shape of the third tube part 103 cut by a plane perpendicular to the longitudinal direction of the third tube part 103 is a circular shape. When the outer diameter of the second tube part 102 is ϕ21 and the outer diameter of the third tube part 103 is ϕ31, it is ϕ21>ϕ31. Moreover, the outer diameter ϕ11 of the first tube part is reduced toward the second bending part 105 side from the first bending part 104 side.

For example, the first tube part 101 includes a narrowing part 106 the outer diameter of which is largely changed between the first bending part 104 and the second bending part 105. In the first tube part 101, the outer diameter φ11 of a second portion 101*b* placed between the narrowing part 106 and the second bending part 105 is smaller than that of a first portion 101*a* placed between the narrowing part 106 and the first bending part 104. When the third tube part 103 is immersed in liquid 39 (see FIG. 9), the second portion 101*b* is disposed at the position overlapping with the liquid surface. Consequently, compared to when the first portion 101*a* is disposed at the position overlapping with the liquid surface, it is possible to reduce the size of a meniscus 39*m*.

When the inner diameter of the second tube part 102 is φ22 and the inner diameter of the third tube part 103 is φ32, it is φ22>φ32. Moreover, the inner diameter φ12 of the first tube part 101 is reduced toward the second bending part 105 side from the first bending part 104 side. In the first tube part 101, the inner diameter φ12 of the second portion 101*b* is smaller than that of the first portion 101*a*.

Figure 8:
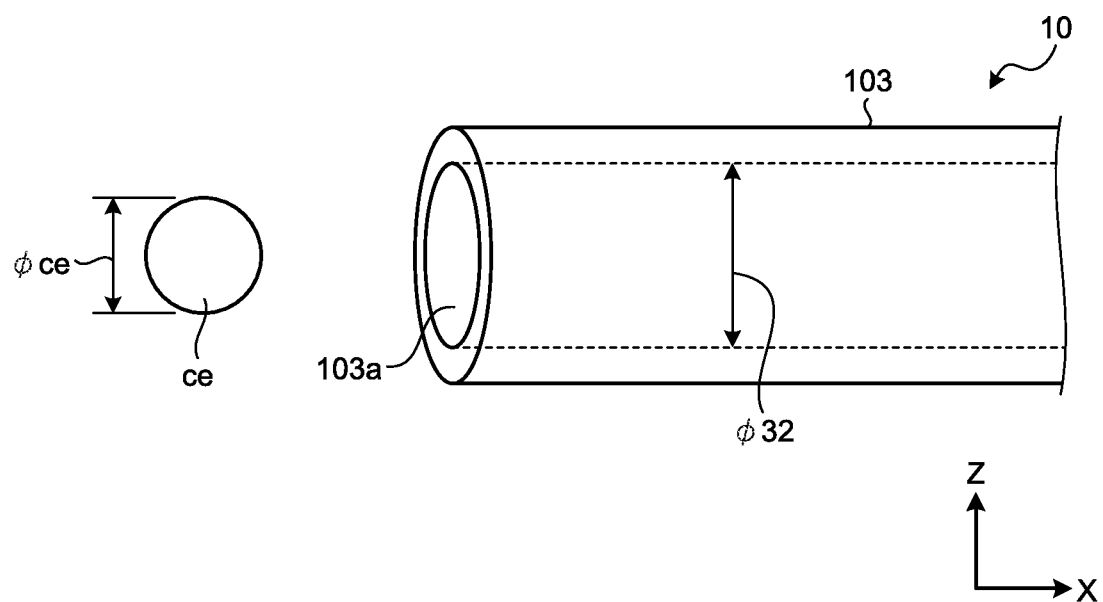
FIG. 8 is an enlarged view of a third tube part of the collection pipette according to the embodiment.

FIG. 8 is an enlarged view of a third tube part of the collection pipette according to the embodiment. As illustrated in FIG. 8, an opening part 103*a* is provided at the tip end of the third tube part 103. The size of the inner diameter φ32 of the third tube part 103 is substantially constant between the opening part 103*a* and the second bending part 105. When the diameter of a cell ce to be collected by the collection pipette 10 is φce, it is preferable that φ32 be larger than φce by about few micrometers. Consequently, the collection pipette 10 can introduce the cell ce into the third tube part 103.

In the collection pipette 10, it is preferable that the size of the bending angles θ1 and θ2, and the forming position of the first bending part 104 and the second bending part 105 be designed so that the third tube part 103 can be placed at the center of the container 38 (FIG. 2) when the manipulation system 100 collects the cell ce.

Figure 9:
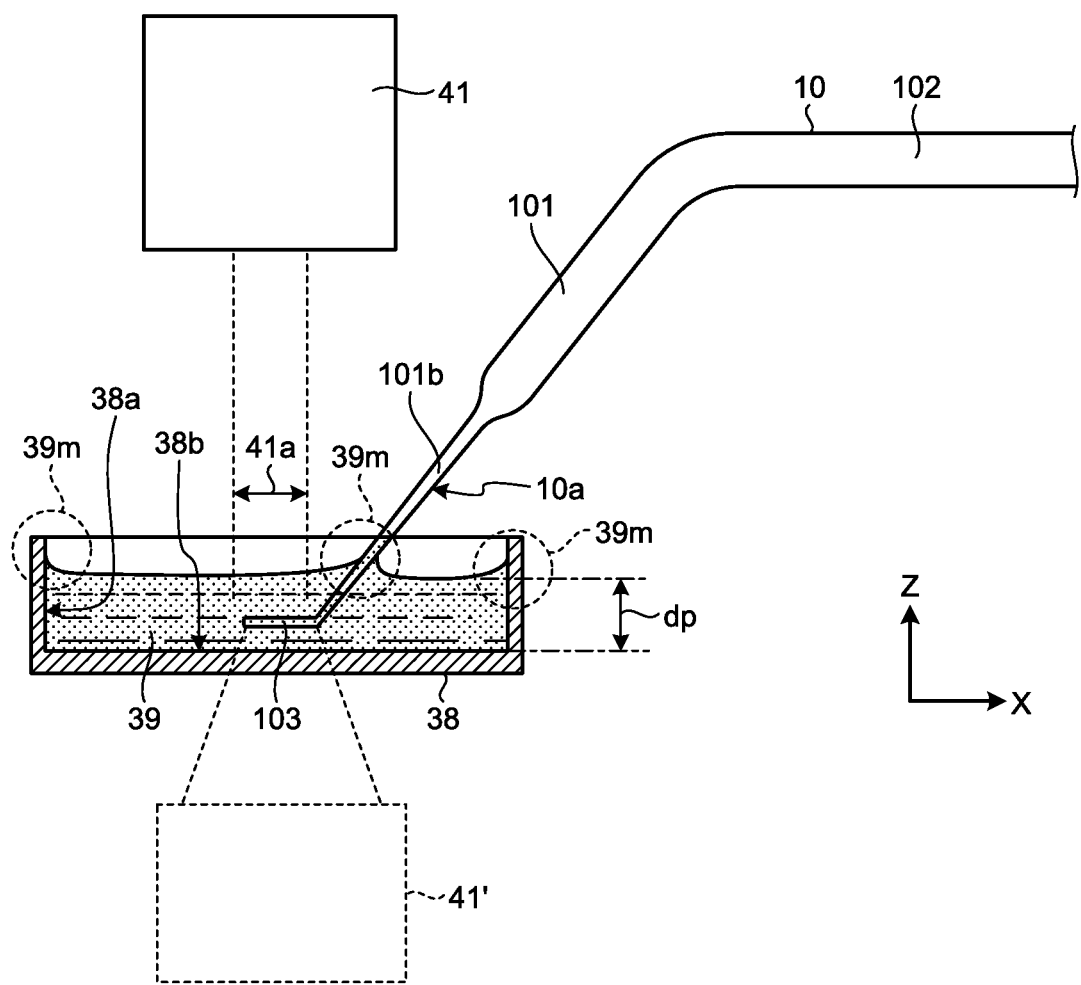
FIG. 9 is a schematic view illustrating a positional relation among the visual field of a first microscope, the collection pipette, and a meniscus.

FIG. 9 is a schematic view illustrating a positional relation among the visual field of the first microscope, the collection pipette, and the meniscus. As illustrated in FIG. 9, when the container 38 holds the liquid 39, the meniscus 39*m* is generated at the boundary between an inner wall surface 38*a* of the container 38 and the liquid surface. Moreover, when the collection pipette 10 is disposed inside the container 38, the meniscus 39*m* is also generated at the boundary between a surface 10*a* of the collection pipette 10 and the liquid surface. The meniscus 39*m* is formed such that the meniscus 39*m* is curved along the inner wall surface 38*a* of the container 38 and the surface 10*a* of the collection pipette 10.

In the manipulation system 100, the entire third tube part 103 can be immersed in the liquid 39, in a state that the third tube part 103, which is the tip end part of the collection pipette 10, is in parallel with a bottom surface 38*b* of the container 38. In this case, the meniscus 39*m* is generated on the surface of the second portion 101*b* away from the third tube part 103, instead of the surface of the third tube part 103. Consequently, it is possible to prevent the meniscus 39*m* from entering a visual field 41*a* of the first microscope 41, and the operator can clearly observe the tip end of the collection pipette 10. For example, because the meniscus 39*m* does not enter the visual field of the first microscope 41, the first microscope 41 can be easily focused on the third tube part 103.

Figure 10:
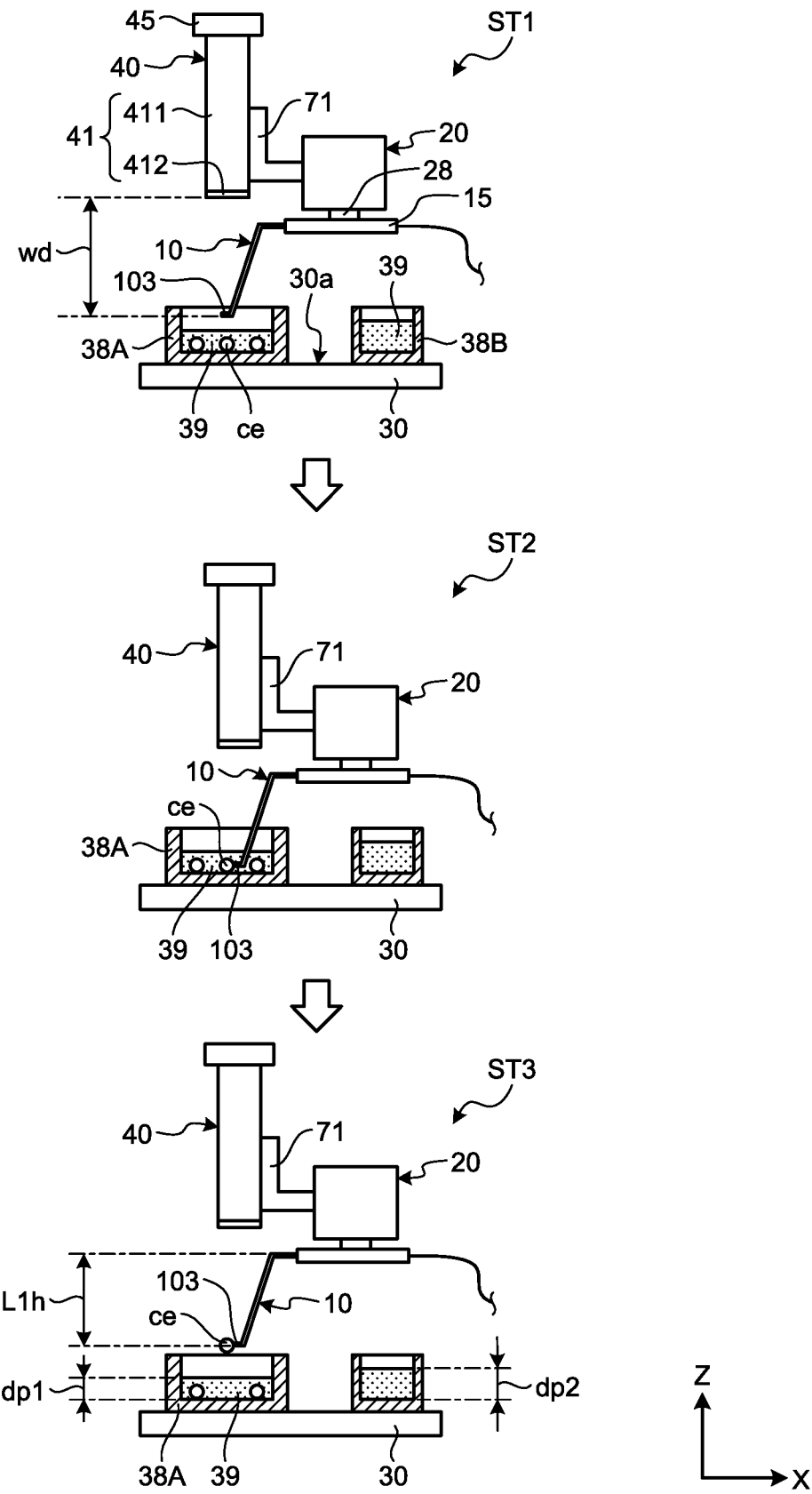
FIG. 10 is a schematic view illustrating an operation example of the manipulation system according to the embodiment.
Figure 11:
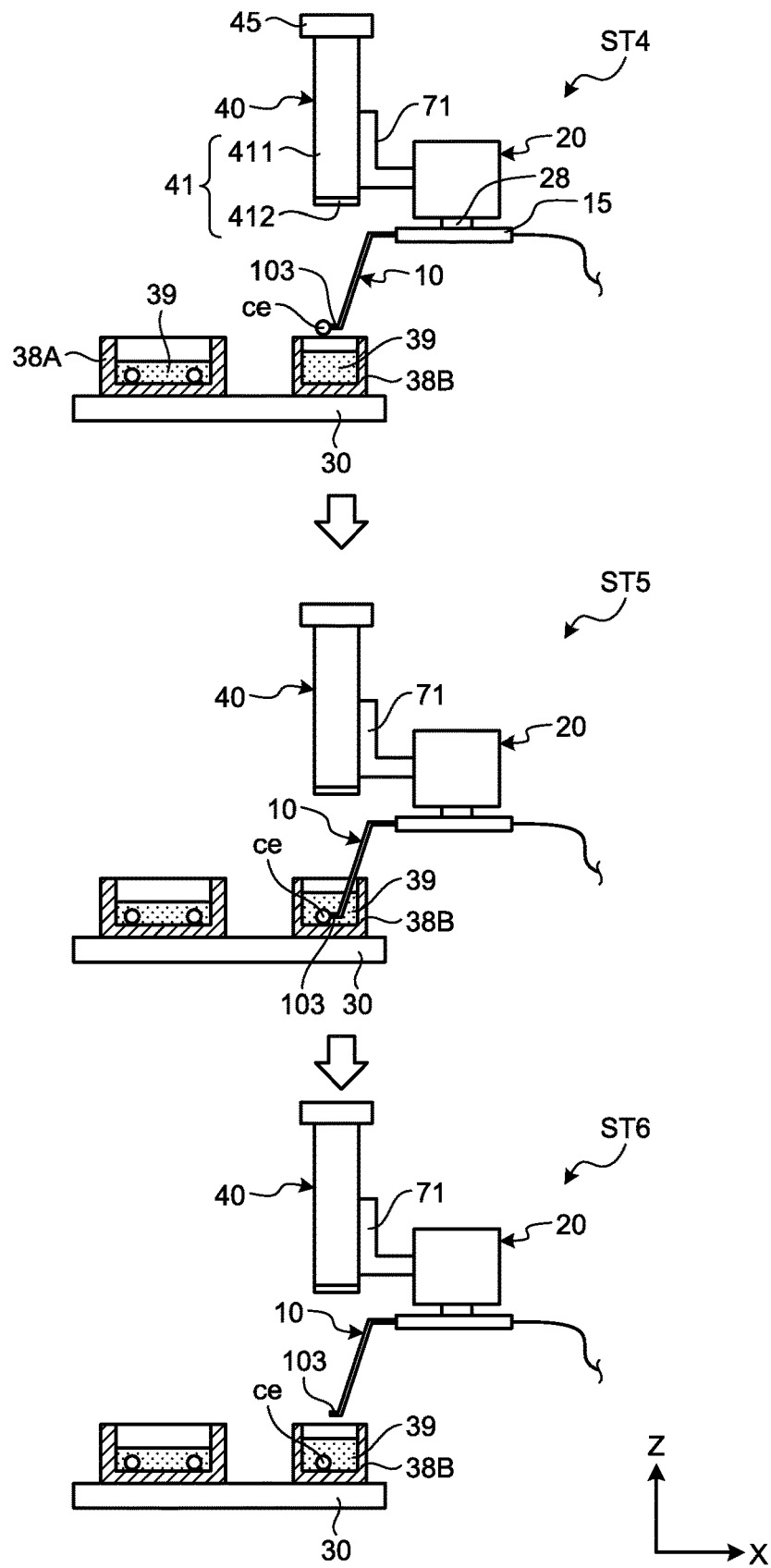
FIG. 11 is a schematic view illustrating an operation example of the manipulation system according to the embodiment.

Next, an operation example of the manipulation system will be described. FIG. 10 and FIG. 11 are each a schematic view illustrating an operation example of the manipulation system according to the embodiment. As illustrated in FIG. 10 and FIG. 11, in the present operation examples, it is assumed that a first container 38A and a second container 38B are mounted on the mounting surface 30*a* of the sample stage 30 respectively, as the container 38. An example when the manipulation system 100 separates the cell ce from the first container 38A to the second container 38B will be described. In FIG. 10 and FIG. 11, the diameter of the cell ce is described larger than the outer diameter of the collection pipette 10. However, this is to clearly indicate the cell ce. In reality, it is preferable that the diameter φce of the cell ce be smaller than the inner diameter φ32 of the collection pipette 10 (see FIG. 8).

At step ST1 in FIG. 10, the collection pipette 10 is fitted to the manipulator 20 with the pipette holding unit 15. The third tube part 103 of the collection pipette 10 is disposed immediately below the objective lens 412 of the first microscope 41. Moreover, the longitudinal direction of the third tube part 103 of the collection pipette 10 is in parallel to the mounting surface 30*a*. At step ST1, the first container 38A holds the liquid 39 and the cells ce. The second container 38B only holds the liquid 39.

In the state described above, in the manipulation system 100, the first microscope 41 is focused on the third tube part 103 of the collection pipette 10. For example, the operator operates the joy stick 57 or the input unit 58 (see FIG. 2), and instructs the controller 50 (see FIG. 2) to initialize the first microscope unit 40. Upon receiving the instruction, the controller 50 sends the driving signal Vz1 (see FIG. 2) to the driving device 414, and moves the objective lens 412 in the Z-axis direction. Consequently, the first microscope 41 of the first microscope unit 40 is focused on the third tube part 103.

Next, in the manipulation system 100, the collection pipette 10 is lowered toward the bottom surface of the first container 38A, and the cell ce is collected by the tip end of the third tube part 103 (step ST2). For example, the operator selects a desirable cell ce among the cells ce held in the first container 38A, while viewing the image displayed on the display unit 80. Next, the operator operates the joy stick 57 or the input unit 58, lowers the collection pipette 10 toward the bottom surface of the first container 38A, and moves the collection pipette 10 in the horizontal direction according to the needs. Consequently, the operator moves the tip end of the third tube part 103 so as to be adjacent to the desirable cell ce. The collection pipette 10 is moved when the controller 50 sends the driving signals Vxy2 and Vz2 (see FIG. 2) to the driving devices 26 and 27 of the manipulator 20.

Next, the operator operates the joy stick 57 or the input unit 58, and makes the collection pipette 10 to suck in the desirable cell ce. The cell ce is sucked when the controller 50 sends the driving signal Vmp (see FIG. 2) to the electric micropump 29 of the manipulator 20, drives the electric micropump 29, and makes the internal pressure of the collection pipette 10 lower than the external pressure of the collection pipette 10. When the internal pressure of the collection pipette 10 is lowered than the external pressure, the desirable cell ce is sucked into the collection pipette 10 with the liquid 39 through the opening part 103*a* (see FIG. 8) provided at the tip end of the third tube part 103.

Next, in the manipulation system 100, the collection pipette 10 is moved upward, and the third tube part 103 is moved to the outside of the first container 38A (step ST3). For example, the operator operates the joy stick 57 or the input unit 58 while viewing the image displayed on the display unit 80, and moves the collection pipette 10 upward to the preset position. The collection pipette 10 is moved upward, when the controller 50 sends the driving signal Vz2 to the driving device 27 of the manipulator 20. It is to be noted that at step ST3, the electric micropump 29 may keep reducing the pressure inside the collection pipette 10 so that the liquid 39 and the cell ce will not flow out from the opening part 103a at the tip end of the third tube part 103.

Next, in the manipulation system 100, the collection pipette 10 is moved from above the first container 38A to above the second container 38B (step ST4). For example, the operator operates the joy stick 57 or the input unit 58 while viewing the image displayed on the display unit 80, and moves the sample stage 30 in the horizontal direction. Consequently, the operator disposes the second container 38B immediately below the third tube part 103. The sample stage 30 is moved when the controller 50 sends the driving signal Vxy3 (see FIG. 2) to the driving device 36 of the sample stage 30.

Next, in the manipulation system 100, the collection pipette 10 is lowered toward the bottom surface of the second container 38B, and the third tube part 103 is moved to the inside of the second container 38B. Then, in the manipulation system 100, the cell ce held inside the collection pipette 10 is discharged to the inside of the second container 38B (step ST5). For example, the operator operates the joy stick 57 or the input unit 58 while viewing the image displayed on the display unit 80, lowers the collection pipette 10 toward the bottom surface of the second container 38B, and moves the collection pipette 10 in the horizontal direction according to the needs. Consequently, the operator moves the third tube part 103 to the inside of the second container 38B. The collection pipette 10 is moved when the controller 50 sends the driving signals Vxy2 and Vz2 to the driving devices 26 and 27 of the manipulator 20.

Next, the operator operates the joy stick 57 or the input unit 58, and discharges the cell ce from the collection pipette. The cell ce is discharged when the controller 50 sends the driving signal Vmp to the electric micropump 29 of the manipulator 20, drives the electric micropump 29, and makes the internal pressure of the collection pipette 10 higher than the external pressure of the collection pipette 10. When the internal pressure of the collection pipette 10 is higher than the external pressure, the cell ce is discharged from the inside of the collection pipette 10 with the liquid 39 through the opening part 103a (see FIG. 8) provided at the tip end of the third tube part 103. It is to be noted that at step ST5, the electric micropump 29 may keep reducing the internal pressure of the collection pipette 10 until immediately before the third tube part 103 reaches inside of the second container 38B.

Next, in the manipulation system 100, the collection pipette 10 is moved upward, and the third tube part 103 is moved to the outside of the second container 38B (step ST6). For example, the operator operates the joy stick 57 or the input unit 58 while viewing the image displayed on the display unit 80, and moves the collection pipette 10 upward to the preset position. The collection pipette 10 is moved upward when the controller 50 sends the driving signal Vz2 to the driving device 27 of the manipulator 20.

As described above, the collection pipette 10 of the present embodiment includes the first tube part 101, the second tube part 102 connected to an end of the first tube part 101, and the third tube part 103 connected to the other end of the first tube part 101. The longitudinal direction of the third tube part 103 intersects with the longitudinal direction of the first tube part 101, and is parallel to the longitudinal direction of the second tube part 102. Consequently, when the third tube part 103 is immersed in the liquid 39, it is possible to generate the meniscus 39m on the surface of the first tube part 101, and move the meniscus 39m away from the third tube part 103. Thus, it is possible to prevent the meniscus 39m from entering the visual field 41a of the first microscope 41, and the operator can clearly observe the tip end of the collection pipette 10. Hence, the present embodiment can provide the tubular instrument with high operability.

The manipulation system 100 of the present embodiment includes the collection pipette 10 described above, the manipulator 20 fitted with the collection pipette 10, the sample stage 30 on which the container 38 for holding the cells ce is mounted, the first microscope 41 disposed above the sample stage 30, and the second microscope 61 disposed at the side of the sample stage 30. Consequently, the operator can observe the third tube part 103 from above while enlarging the third tube part 103 by using the first microscope 41. Moreover, the operator can observe the third tube part 103 from the side while enlarging the third tube part 103 by using the second microscope 61. Thus, the operator can more clearly observe the tip end of the collection pipette 10. Hence, the present embodiment can provide the manipulation system 100 with high operability.

Moreover, the manipulation system 100 includes the first image pickup device 45 that picks up an image of the third tube part 103 through the first microscope 41, the second image pickup device 65 that picks up an image of the third tube part 103 through the second microscope 61, the third image pickup device 75, and the display unit 80. The third image pickup device 75 picks up an image of the sample stage 30 side from the direction (third direction) intersecting with the Z-axis direction (first direction) picked up by the first image pickup device 45 and the Y-axis direction (second direction) picked up by the second image pickup device 65. The display unit 80 displays the first image 811 picked up by the first image pickup device 45, the second image 812 picked up by the second image pickup device 65, and the third image 813 picked up by the third image pickup device 75. Consequently, the display unit 80 can display the first image 811 that indicates the enlarged third tube part 103 from above, the second image 812 that indicates the enlarged third tube part 103 from the side, and the third image 813 that is a bird's eye view of the sample stage 30 and the surroundings, by arranging the first image 811, the second image 812, and the third image 813 side by side on the single screen 81.

Furthermore, the manipulation system 100 includes the storage unit 56 that stores therein the first image 811, the second image 812, and the third image 813 in an associated manner on the basis of the image pickup time. Consequently, the display unit 80 can reproduce and display side by side the first image 811, the second image 812, and the third image 813 that are picked up at the same time.

As illustrated in FIG. 10, to certainly move the cell ce while moving the cell ce, it is preferable that the operator continuously observe the third tube part 103, which is the tip end of the collection pipette 10, from step ST1 to step ST6. To accomplish the above, the microscope 40 can observe the collection pipette 10 from above. Moreover, the focal distance wd of the microscope 40 is greater than the crank height L1h or the crank length L1 (see FIG. 6) of the collection pipette 10. Furthermore, the narrowed length L1' of the collection pipette 10 (see FIG. 6) is longer than the depth dp1 or the depth dp2 of the liquid surface. The device configuration of the manipulation system 100 of the present embodiment is formed in this manner.

The crank height L1h is the height of the collection pipette 10 in the Z-axis direction. Moreover, in the first portion 101, the narrowed length L1' is the length of a portion the diameter of which is equal to or less than about two times of the outer diameter ϕ31 of the third tube part 103. For example, the narrowed length L1' is the length of the second portion 101b placed between the narrowing part 106 and the second bending part 105. The depth dp1 of the liquid surface is the depth of the liquid surface in the first container 38A. The depth dp2 of the liquid surface is the depth of the liquid surface in the second container 38B.

In general, because image pickup is important in observing cells, the image pickup is performed from below the container (for example, a petri dish) holding the cells. In other words, in general, an inverted microscope 41' is disposed at the position below the container 38 in FIG. 9, and the cells are observed from below by the inverted microscope 41'. However, when the inverted microscope method is used for observation, the pipette and the cells can only be confirmed at step ST2 and step ST5, and it is difficult to guarantee the certainty (admissibility) of moving cells. When the cells are observed from above, an interface between the liquid and the pipette is present in the optical path of the microscope. Thus, distortion occurs in the image due to the refraction of the interface, thereby making the observation difficult. Consequently, in the present embodiment, the diameter of the second portion 101b, which is a narrowed part, is narrowed sufficiently, and the narrowed length L1' is made longer than the depth dp (see FIG. 9) of the liquid surface. Thus, it is possible to reduce the size of the meniscus of the interface, and prevent the observation from being obstructed. During the observation, the transparency of liquid does not affect the depths dp1 and dp2 of the liquid surface, with reduction in the depths dp1 and dp2. However, when the liquid amount is too small, the liquid surface does not extend uniformly. Thus, it is preferable to define the depths dp1 and dp2 of the liquid surface so that the liquid amount can be between the minimum liquid amount (V1) at which the liquid surface extends uniformly and twice the amount (2V1). By having such a configuration, the present embodiment can observe cells and guarantee the admissibility of moving cells.

The collection pipette 10 and the manipulation system 100 of the present embodiment have been described above. However, the present embodiment is not limited to the contents described above. For example, in the present embodiment, the first microscope 41 is the stereoscopic microscope in which the objective lens 412 is placed above the container 38. However, in the present embodiment, the first microscope 41 may also be the inverted microscope in which the objective lens 412 is placed below the container 38. The collection pipette 10 and the manipulation system 100 of the present embodiment are applicable either when the first microscope 41 is the stereoscopic microscope described above or the inverted microscope.

REFERENCE SIGNS LIST 1 base
2, 3, 4 fixing tool
10 collection pipette
15 pipette holding unit
20 manipulator
26, 27, 36, 63 driving device
28, 71 coupling unit
29 electric micropump
30 sample stage
38 container
38A first container
38B second container
38a inner wall surface
38b bottom surface
39 liquid
39m meniscus
40 first microscope unit
41 first microscope
41a visual field
45 first image pickup device
58 input unit
60 second microscope unit
61 second microscope
65 second image pickup device
75 third image pickup device
80 display unit
81 screen
100 manipulation system
101 first tube part
102 second tube part
103 third tube part
103a opening part
811 first image
812 second image
813 third image

The invention claimed is:

1. A manipulation system that collects a microscopic object, the manipulation system comprising:
a tubular instrument including:
a first tube part;
a second tube part connected to an end of the first tube part; and
a third tube part connected to another end of the first tube part, wherein a longitudinal direction of the third tube part intersects with a longitudinal direction of the first tube part, and is parallel to a longitudinal direction of the second tube part;
a manipulator fitted with the tubular instrument;
a sample stage on which a container for holding the microscopic object is mounted;
a first microscope disposed above the sample stage;
a second microscope disposed at a side of the sample stage;
a first image pickup device that picks up an image of the third tube part provided parallel to a mounting surface of the sample stage, through the first microscope;
a second image pickup device that picks up an image of the third tube part provided parallel to a mounting surface of the sample stage, through the second microscope;
a third image pickup device that picks up an image of a side of the sample stage from a third direction that intersects with a first direction picked up by the first image pickup device and a second direction picked up by the second image pickup device;
a display unit that displays a first image picked up by the first image pickup device, a second image picked up by the second image pickup device, and a third image picked up by the third image pickup device; and
a storage unit that stores therein the first image, the second image, and the third image in an associated manner based on an image pickup time.

2. The manipulation system according to claim 1, wherein a length in the longitudinal direction of the third tube part is shorter than that in the longitudinal direction of the first tube part.

3. The manipulation system according to claim 1, wherein the first tube part includes a first portion placed at a side of the end, and a second portion placed at a side of the other end, and an outer diameter of the second portion is smaller than an outer diameter of the first portion.

4. The manipulation system according to claim 1, further comprising:

a coupling unit that couples the manipulator and the first microscope.

* * * * *